United States Patent [19]

Kageyama

[11] Patent Number: 5,030,197
[45] Date of Patent: Jul. 9, 1991

[54] APPARATUS FOR DRIVING BLOOD PUMP

[75] Inventor: Toshinobu Kageyama, Okazaki, Japan

[73] Assignees: Aisin Seiki Kabushiki Kaisha, Kariya; Kabushiki Kaisha Shinsangyokaihatsu, Tokyo, both of Japan

[21] Appl. No.: 468,877

[22] Filed: Jan. 23, 1990

[30] Foreign Application Priority Data

Jan. 31, 1989 [JP] Japan .................. 1-023443

[51] Int. Cl.⁵ ............................................. A61B 19/00
[52] U.S. Cl. ...................................... 600/17; 600/16; 623/3
[58] Field of Search ................ 600/16, 17, 18; 623/3; 128/672, 673

[56] References Cited

U.S. PATENT DOCUMENTS

4,546,760 10/1985 Suzuki et al. .......................... 600/16
4,556,997 12/1985 Takamiya et al. .................... 600/16
4,648,385 3/1987 Oumi et al. ........................... 600/17
4,934,996 6/1990 Mohl et al. ........................... 600/17

Primary Examiner—Lee S. Cohen
Assistant Examiner—Kennedy J. Schaetzle
Attorney, Agent, or Firm—Burns, Doane, Swecker & Mathis

[57] ABSTRACT

An apparatus for driving a blood pump such as an artificial pump. The apparatus comprises a pressure pulse generator for producing pressure pulses, a pressure detector for detecting the pressure produced by the pressure pulse generator, and an electrical control unit (ECU) consisting of a microcomputer. The ECU estimates the pressure range obtained after the pressure is switched from a positive value to a negative value or vice versa, from the pressure obtained before the pressure is switched. The ECU then compares the pressure obtained after the switch of the pressure with the pressure range to determine whether the pressure is abnormal or not.

2 Claims, 7 Drawing Sheets

P. P. S. = POSITIVE PRESSURE SOURCE
N. P. S. = NEGATIVE PRESSURE SOURCE

| FLAG | | CONTENTS |
|---|---|---|
| USED FOR THE APPARATUS ASSISTING THE LEFT HEART | LP | PRESENT PRESSURE VALUE |
| | LNPS | SET NEGATIVE PRESSURE |
| | LPPS | SET POSITIVE PRESSURE |
| | LNPM | NEGATIVE PRESSURE VALUE IMMEDIATELY BEFORE PRESSURE IS SWITCHED FROM NEGATIVE TO POSITIVE VALUE |
| | LPPM | POSITIVE PRESSURE VALUE IMMEDIATELY BEFORE PRESSURE IS SWITCHED FROM POSITIVE TO NEGATIVE VALUE |
| | LrefP | POSITIVE PRESSURE-CORRECTING VALUE |
| | LrefN | NEGATIVE PRESSURE-CORRECTING VALUE |
| | LCNT 20 | TIME FOR WHICH NEGATIVE PRESSURE IS APPLIED BEFORE PRESSURE IS SWITCHED FROM NEGATIVE TO POSITIVE VALUE |
| | LAP2 | PRESSURE OBTAINED WHEN MEASUREMENT IS CHECKED |
| USED FOR THE APPARATUS ASSISTING THE RIGHT HEART | RP | PRESENT PRESSURE VALUE |
| | RNPS | SET NEGATIVE PRESSURE VALUE |
| | RPPS | SET POSITIVE PRESSURE VALUE |
| | RNPM | NEGATIVE PRESSURE VALUE IMMEDIATELY BEFORE PRESSURE IS SWITCHED FROM NEGATIVE TO POSITIVE VALUE |
| | RPPM | POSITIVE PRESSURE VALUE IMMEDIATELY BEFORE PRESSURE IS SWITCHED FROM POSITIVE TO NEGATIVE VALUE |
| | RrefP | POSITIVE PRESSURE-CORRECTING VALUE |
| | RrefN | NEGATIVE PRESSURE-CORRECTING VALUE |
| | RCNT 20 | TIME FOR WHICH NEGATIVE PRESSURE IS APPLIED BEFORE PRESSURE IS SWITCHED FROM NEGATIVE TO POSITIVE VALUE |
| | RAP2 | PRESSURE OBTAINED WHEN MEASUREMENT IS CHECKED |
| ABLNC | | COUNTER FOR COUNTING THE NUMBER OF SUCCESSIVE ABNORMAL NEGATIVE PRESSURE VALUES FOR THE LEFT HEART ; NORMAL = 5 |
| ABRNC | | COUNTER FOR COUNTING THE NUMBER OF SUCCESSIVE ABNORMAL NEGATIVE PRESSURE VALUES FOR THE RIGHT HEART ; NORMAL = 5 |
| ABLPC | | COUNTER FOR COUNTING THE NUMBER OF SUCCESSIVE ABNORMAL POSITIVE PRESSURE VALUES FOR THE LEFT HEART ; NORMAL = 5 |
| ABRPC | | COUNTER FOR COUNTING THE NUMBER OF SUCCESSIVE ABNORMAL POSITIVE PRESSURE VALUES FOR THE RIGHT HEART ; NORMAL = 5 |
| PAA | | FLAG USED TO MAKE A DECISION AS TO WHETHER THE PRESSURE IS ABNORMAL ; NORMAL = 0 |

APPARATUS FOR DRIVING BLOOD PUMP

FIELD OF THE INVENTION

The present invention relates to an apparatus for driving a blood pump such as a perfectly artificial heart, auxiliary artificial heart, or balloon pump by means of pressure pulses.

BACKGROUND OF THE INVENTION

A blood pump assists the action of the heart of a patient whose circulatory system has failed. Therefore, if the function of the apparatus driving the blood pump stops, the patient will be adversely affected. If a perfectly artificial heart fails, then the function of the heart is completely lost. If an auxiliary artificial heart or a balloon pump fails, burden is suddenly imposed on the patient's weakened heart.

Accordingly, the frequency of troubles in blood pumps and driving apparatuses must be reduced. To cope with troubles in driving apparatuses, various means have been proposed. An apparatus disclosed in Japanese Patent Laid-Open No. 136,352/1983 incorporates a battery and a pressure tank to make preparations for disconnection from an external power supply. An apparatus disclosed in Japanese Patent Laid-Open No. 207,668/1985 is equipped with a plurality of pressure sensors to monitor the waveform of pressure. In the techniques disclosed in Japanese Patent Laid-Open Nos. 169,463/1983 and 249,655/1987, two pressure-generating devices are mounted. If one of them fails, it can be switched to the other.

The prior art method of detecting trouble in a driving apparatus consists in detecting the output pressure, comparing the detected pressure with a preset pressure, and regarding the apparatus as defective if there is a great difference between them. For example, in the techniques disclosed in Japanese Patent Laid-Open No. 249,655/1987, the period of pressure pulses and the level of pressure are checked.

In order to drive the blood pump according to the condition of the organism, it is necessary that the period or the duty cycle of pressure pulses can be varied. Accordingly, where a check is done to see if the pressure pulses are abnormal, it is necessary to determine the time at which the pressure is checked, considering the minimum period, the minimum duty cycle, and the maximum duty cycle that can be set.

Since the pressure pulses delivered from a driving apparatus have positive pressure and negative pressure alternately, immediately after the pressure is switched from the negative pressure to the positive pressure, the pressure does not rise quickly. Also, immediately after the pressure is switched from the positive pressure to the negative pressure, the pressure does not drop rapidly. Therefore, it takes long for the pressure to reach the set value after the pressure is switched to the negative or positive pressure. This time varies, depending on the pressure obtained before the pressure is switched, on the time for which the negative pressure is applied, and on the time for which the positive pressure is applied. For example, when the pressure is switched from a negative pressure to a positive pressure, if the negative pressure obtained before the pressure is switched is large, it takes a long time for the pressure to settle down to the preset positive value. Conversely, if the negative pressure obtained before the pressure is switched is small, then the pressure quickly rises to the preset positive value after the pressure is switched.

Because the waveform of the pressure is blunted in this way, when the pressure is checked, the pressure is not stable and so the detected pressure may deviate from the preset pressure. In some cases, if the driving apparatus is normal, it may be regarded as defective. Where the driving apparatus is used for a patient suffering from serious cardiac insufficiency, the operation of the apparatus should not fluctuate at all in normal condition.

SUMMARY OF THE INVENTION

Accordingly, it is an object of the present invention to provide a blood pump-driving apparatus producing pressure pulses which can be accurately, precisely, and reliably judged whether they are abnormal or not under every operating condition.

The above object is achieved by a blood pump-driving apparatus comprising: a pressure pulse generator for producing pressure pulses; a pressure-detecting means for detecting the pressure produced by the pressure pulse generator; an estimating means which reads the output value from the pressure-detecting means before the pressure of the pressure pulses is switched to other value and estimates the range of pressures obtained after the switch of the pressure either from said output value or from the time for which the pressure was applied; and a determining means which compares the output value produced from the pressure-detecting means after the switch of the pressure with the pressure range and determines whether the pressure is abnormal.

In this apparatus, the pressure range used to determine whether the pressure is abnormal is estimated either from the pressure obtained before the switch of the pressure or from the time for which the previous pressure was applied. Therefore, the pressure produced at the time of the switch of the pressure can be estimated, irrespective of the pressure generated immediately before the switch of the pressure. Thus, if the pressure pulses are blunted, no abnormality is detected as long as the pressure pulse generator is not at fault.

Other objects and features of the invention will appear in the course of the description thereof which follows.

BRIEF DESCRIPTION OF THE DRAWINGS

FIG. 9 is a table illustrating the flags used in the flowchart of FIG. 2.

DETAILED DESCRIPTION OF THE INVENTION

Figure 1:
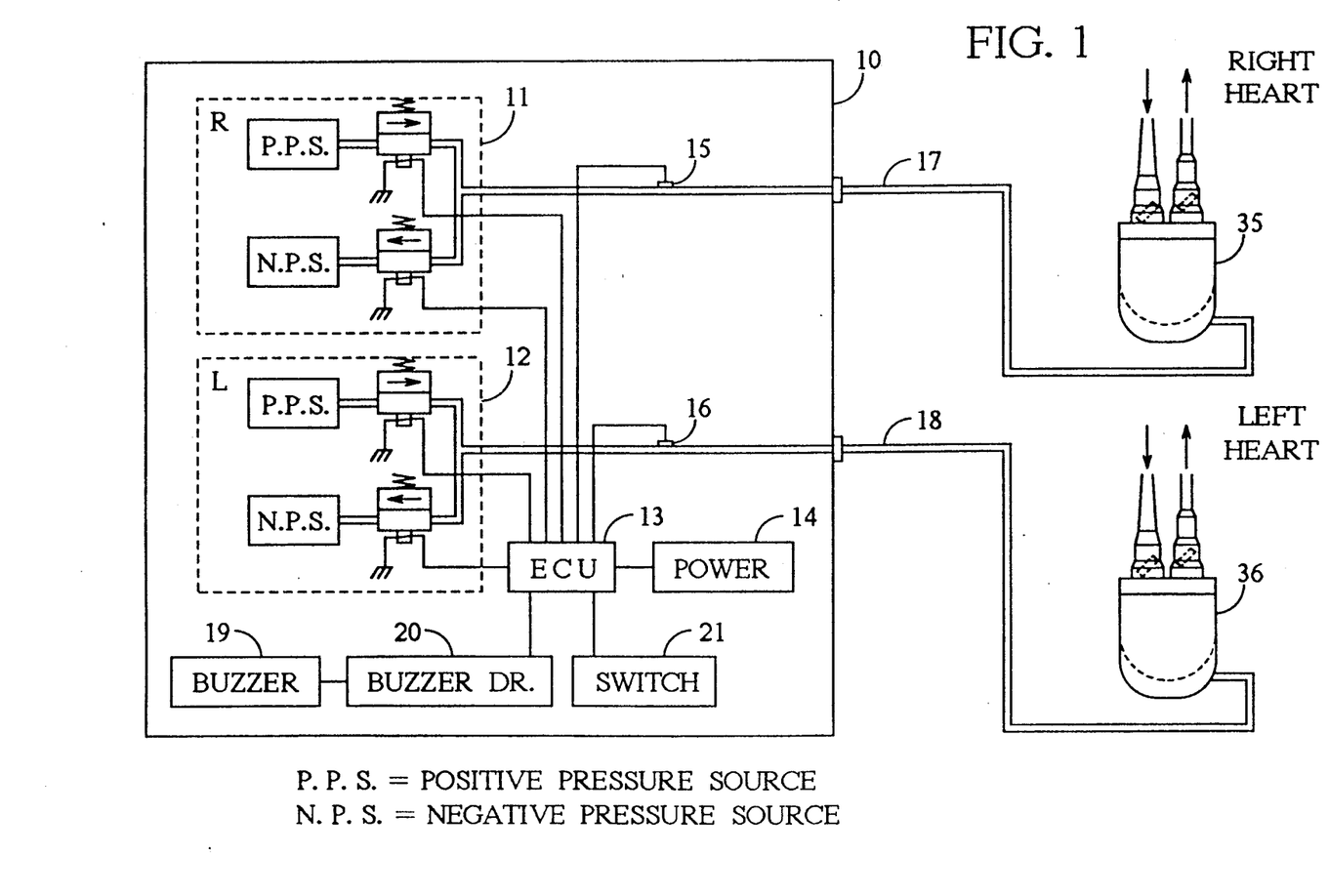
FIG. 1 is a circuit diagram of an apparatus according to the invention.

Referring to FIG. 1, a blood pump-driving apparatus 10 comprises a pressure pulse generator 11 for producing pressure pulses for the right heart, another pressure pulse generator 12 for producing pressure pulses for the left heart, an electrical control unit (ECU) 13 for controlling the pulse generators 11 and 12, a power supply 14 for the electrical control unit 13, an operation switch 21 for setting a value for controlling the apparatus 10, a pressure detector 15 for detecting the pressure produced by the pulse generator 11, and a pressure detector 16 for detecting the pressure produced by the pressure generator 12. The electrical control unit 13 controls the two pulse generators 11 and 12 according to information, such as blood pressure and a cardiogram, about an organism (not shown) in which a blood pump (not shown) has been infixed. The ECU 13 synchronizes the pressure pulses with the pulsation of the organism and controls the pressure according to the condition of the organism. The output pulses from the pulse generator 11 for the right heart are sent to the blood pump via a pipe 17 for the right heart. The output pulses from the pulse generator 12 for the left heart is sent to the blood pump through a pipe 18 for the left heart. Since this blood pump-driving apparatus is similar in structure to the artificial heart-driving apparatus disclosed in Japanese Patent Laid-Open No. 169,460/1983, for the method of producing pressure pulses refer to this Japanese patent bulletin.

The pipe 17 is connected with an artificial heart pump 35 that is a blood pump. The pump 35 is connected with the right atrium and with the pulmonary artery via cannulas. When the pressure inside the pipe 17 increases, the artificial heart pump forces blood into the pulmonary artery. When the pressure decreases, the pump draws blood from the right atrium. Similarly, the pipe 18 is connected with an artificial heart pump 36 that is a blood pump. The pump 36 is connected with the left atrium and also with the main artery via cannulas. When the pressure inside the pipe 18 increases, the artificial heart pump forces blood into the main artery. When the pressure decreases, the pump takes in blood from the left atrium.

Figures 2, 3:
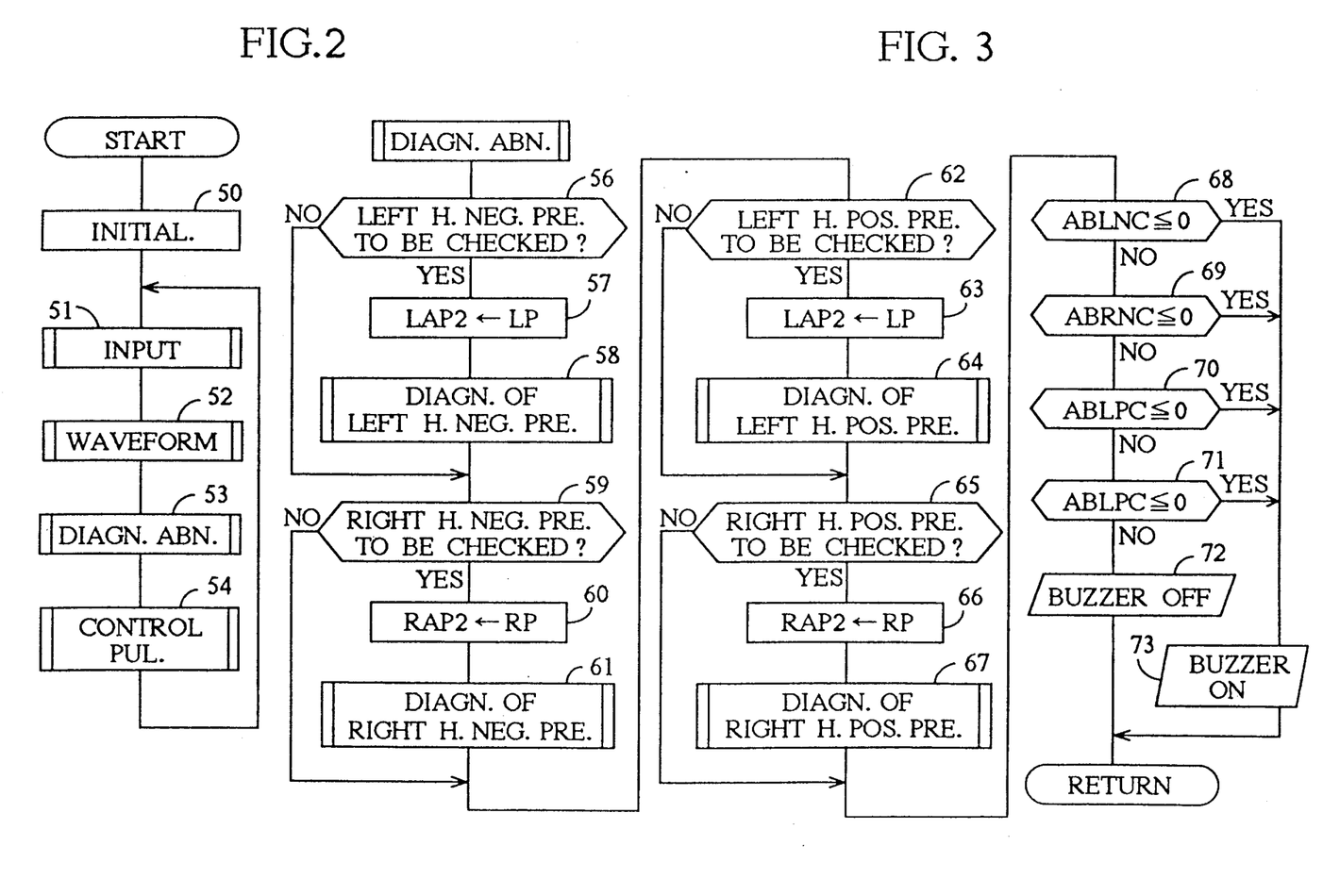
FIG. 2 is a flowchart illustrating the main routine executed by the ECU 13 shown in FIG. 1.
FIGS. 3-7 are flowcharts illustrating the abnormality diagnostic routine illustrated in FIG. 2.

The ECU 13 is a microcomputer in the form of one chip and operates in the manner as illustrated in the flowcharts of FIGS. 2-7. FIG. 2 illustrates the main routine executed by the microcomputer. When the microcomputer is started, its internal memory, input and output terminals are initialized (step 50). Then, a signal input routine (step 51), a waveform display routine (step 52), an abnormality diagnostic routine (step 53), and a pulsation control routine (step 54) are repeated.

In the signal input routine, pressure signals from the pressure detectors 15, 16 are applied to the microcomputer. When the operation switch 21 is operated to set a pressure value, this value is input to the microcomputer also in this routine. The output value from the pressure detector 15 of the pressure pulse generator for assisting the left heart is indicated by LP. The output value from the pressure detector 16 of the pressure pulse generator for assisting the right heart is indicated by RP. The set positive pressure for the left heart, the set positive pressure for the right heart, the set negative pressure for the left heart, and the negative pressure for the right heart are indicated by LPPS, RPPS, LNPS, RNPS, respectively.

In the waveform display routine, various measured values are processed to display waveforms and data on a display device (not shown).

In the abnormality diagnostic routine, a check is done, using measured blood flow rates and pressure values, to see whether the pressure pulse generator is at fault. If it is at fault, the microcomputer performs a processing to cause a buzzer to sound.

In the pulsation control routine, the solenoid valves in the pressure pulse generator are activated according to the measured pressure value or other value to switch the pressure to a different value. In this routine, the time for which a negative pressure is applied to the left heart is substituted into variable LCNT20. The time for which a negative pressure is applied to the right heart is substituted into variable RCNT20.

The abnormality diagnostic routine is next described in detail by referring to FIG. 3. The contents of flags used in FIG. 3 and the following figures are shown in FIG. 9.

Figure 8:
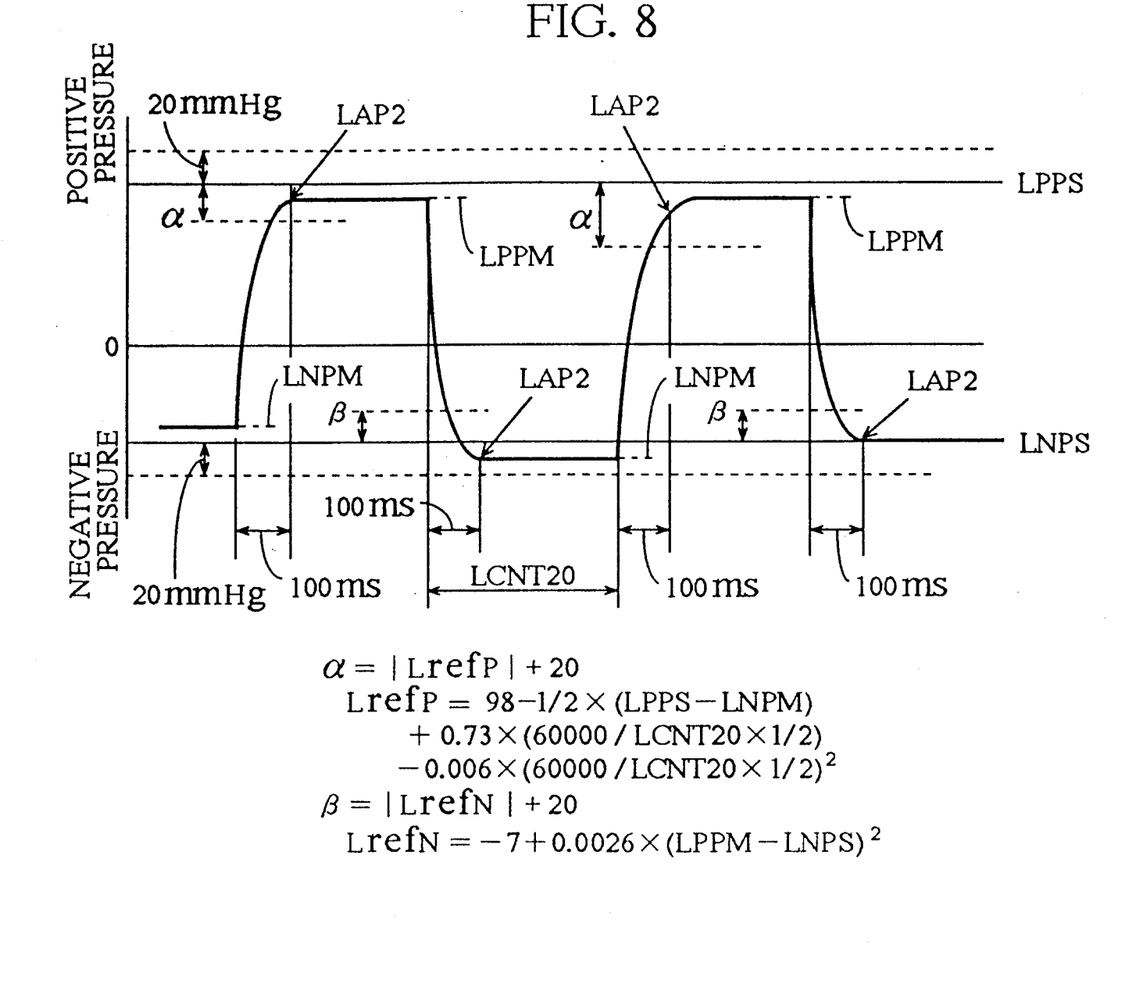
FIG. 8 is a diagram for illustrating the operation of the apparatus shown in FIG. 1.

When the abnormality diagnostic routine is executed, the value of the pressure supplied to the blood pump is checked (steps 56-67). If it is the time to check both positive and negative pressures for the left and right hearts, the diagnosis of the pressure is carried out. The time at which the check is performed is determined by the minimum period of pressure pulses which can be set. For example, if the possible time for which the positive pressure is applied is 100 ms, then the check can be done at any arbitrary instant within 100 ms after the pressure is switched from a negative pressure to a positive pressure. In the present example, as shown in FIG. 8, the positive pressure is checked within 100 ms since the application of the positive pressure. The negative pressure is checked within 100 ms since the application of the negative pressure.

Figure 4:
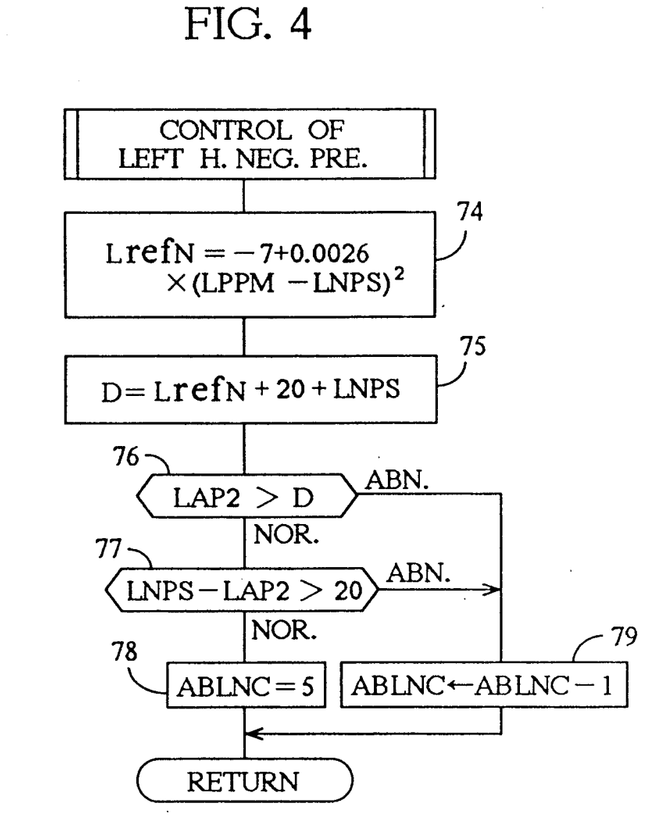

When it is the time to check the negative pressure for the left heart, the present pressure value is substituted into value LAP2, and the left heart negative pressure diagnostic routine is executed. The left heart negative pressure diagnosis is made as illustrated in the flowchart of FIG. 4. First, a negative pressure-correcting value $L_{ref}N$ is calculated from the pressure LPPM obtained immediately before the application of the negative pressure and from a preset negative pressure LNPS, using the following empirical formula.

$$L_{ref}N = -7 - 0.0026 \cdot (LPPM - LNPS)^2 \quad (1)$$

The lower limit D of the normal range of negative pressure values is derived from the correcting value $L_{ref}N$ and given by $$D = L_{ref}N + 20 - LNPS \quad (2)$$

In this equation, "20" means 20 mmHg that is allowance for variations. If the present pressure value LAP2 is less than D and greater than the preset negative value LNPS−20, then the pressure is regarded as normal. If the pressure value LAP2 is larger than D or less than the preset negative value LNPS−20, then the pressure is regarded as abnormal. If the pressure is judged to be normal, value 5 is substituted into a variable ABLNC. If the pressure is judged to be abnormal, the variable ABLNC is decremented. Therefore, if the negative pressure for the left heart is judged to be abnormal at five successive decisions, then the variable ABLNC becomes null.

Figure 5:
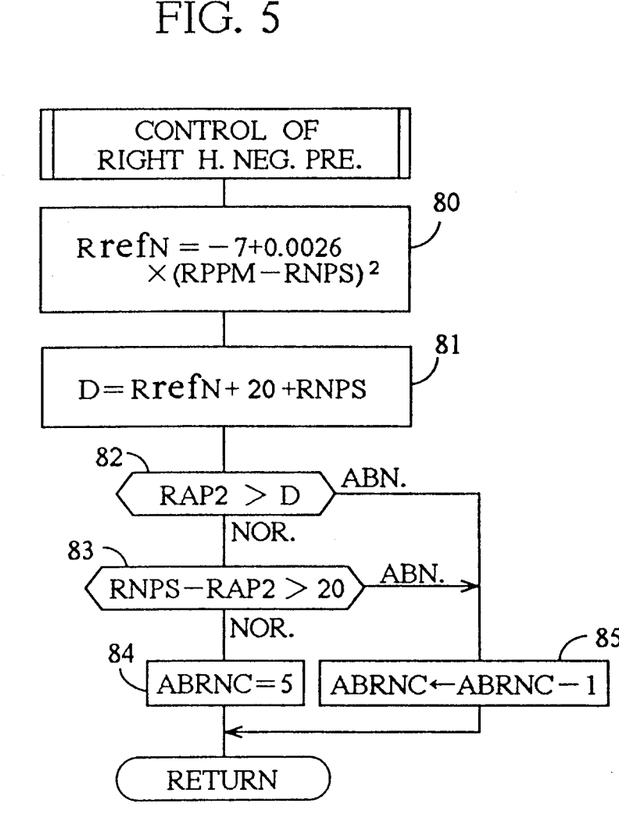

The negative pressure for the right heart is similarly checked. If this negative pressure is normal, the variable ABRNC is equal to 5. If the pressure is judged to be abnormal at five successive decisions, then the variable ABRNC equals 0.

Figure 6:
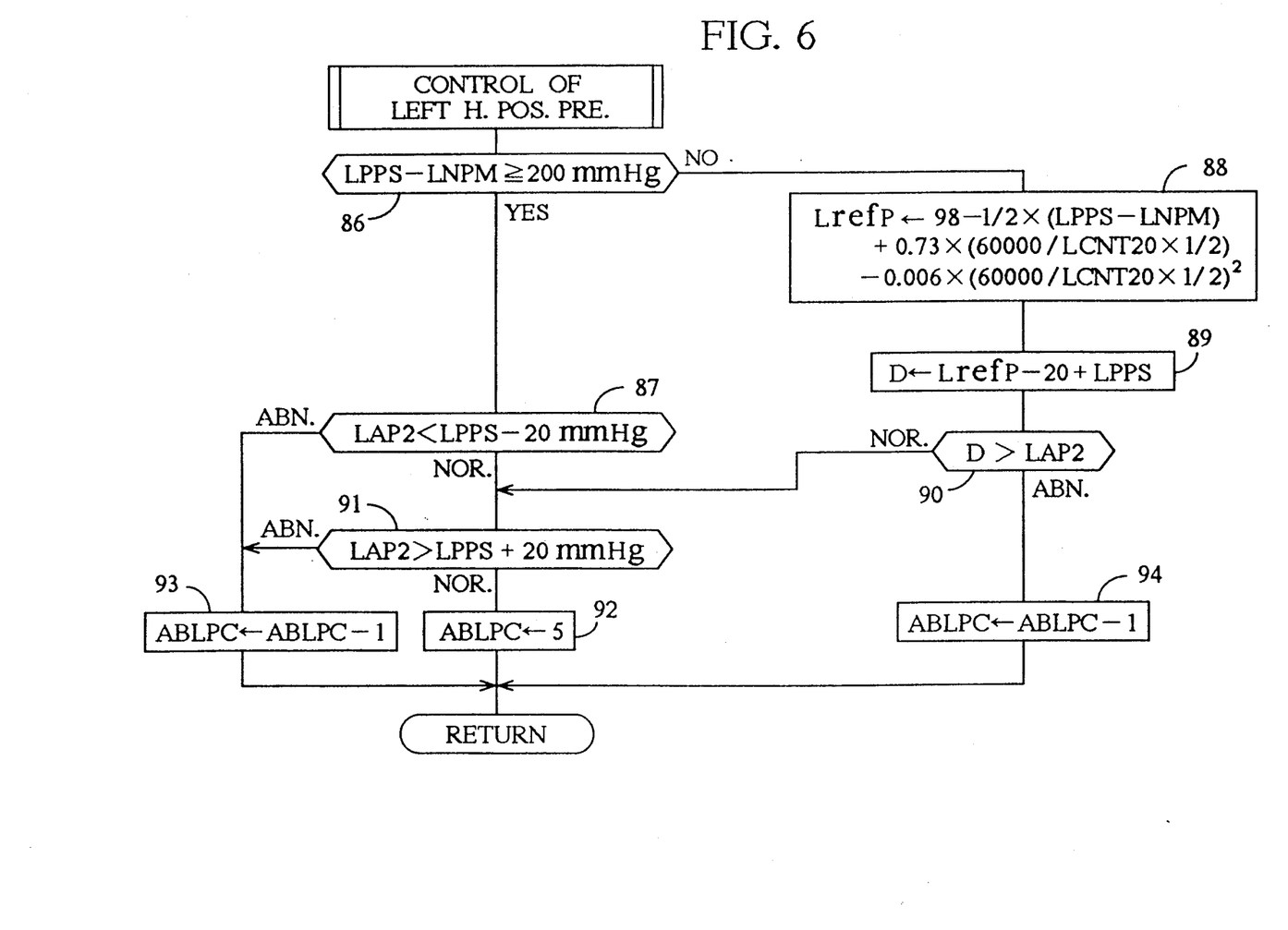

When it is the time to check the positive pressure for the left heart, the present pressure value is substituted into the value LAP2, and the left heart positive pressure diagnostic routine is executed as illustrated in the flowchart of FIG. 6. First, when the preset positive pressure value LPPS minus the negative pressure value LNPM produced immediately before the application of the positive pressure is less than 200 mmHg, if the present pressure value LAP2 is greater than the preset positive value LPPS−20 mmHg, then the pressure is regarded as normal. If it is not so, the pressure is regarded as abnormal. If the sum of the preset positive pressure LPPS and the negative pressure value LNPM obtained immediately before the application of the positive pressure is greater than the normal range by 200 mmHg, then a positive value-correcting value $L_{ref}P$ is calculated from the pressure value LNPM produced immediately before the application of the positive pressure, from the preset positive pressure LPPS, and from the time LCNT20 for which the negative pressure is applied, using the following empirical formula.

$$L_{ref}P = 98 - \tfrac{1}{2} \times (LPPS - LNPM) + 0.73 \times (60000/LCNT20/2) - 0.006 \times (60000/LCNT20/2)^2 \quad (3)$$

The lower limit D of the normal range of positive pressure is calculated from the correcting value $L_{ref}P$ and given by $$D = L_{ref}P - 20 - LPPS \quad (4)$$

In this equation, "20" means 20 mmHg and is allowance for variations. If the present pressure value LAP2 is greater than D, the pressure is regarded as normal. If the pressure value is less than D, the pressure is regarded as abnormal. When the pressure is regarded as normal at the two decisions above, if the present pressure LAD2 is less than the predetermined positive pressure LPPS+20 mmHg, the pressure is regarded as normal. Conversely, if the present value LAP2 is less than LPPS+20 mmHg, then the pressure is regarded as abnormal. If the pressure is regarded as normal, value 5 is substituted into the variable ABLNC. If the pressure is regarded as abnormal, then the variable ABLNC is decremented. Therefore, if the negative pressure for the left heart is regarded as abnormal at five successive decisions, the variable ABLPC is 0. Positive pressure values are classified by the pressure range (LPPS+LNPM). This is because if the pressure range is narrow, the positive pressure-correcting value $L_{ref}P$ is meaningless.

Figure 7:
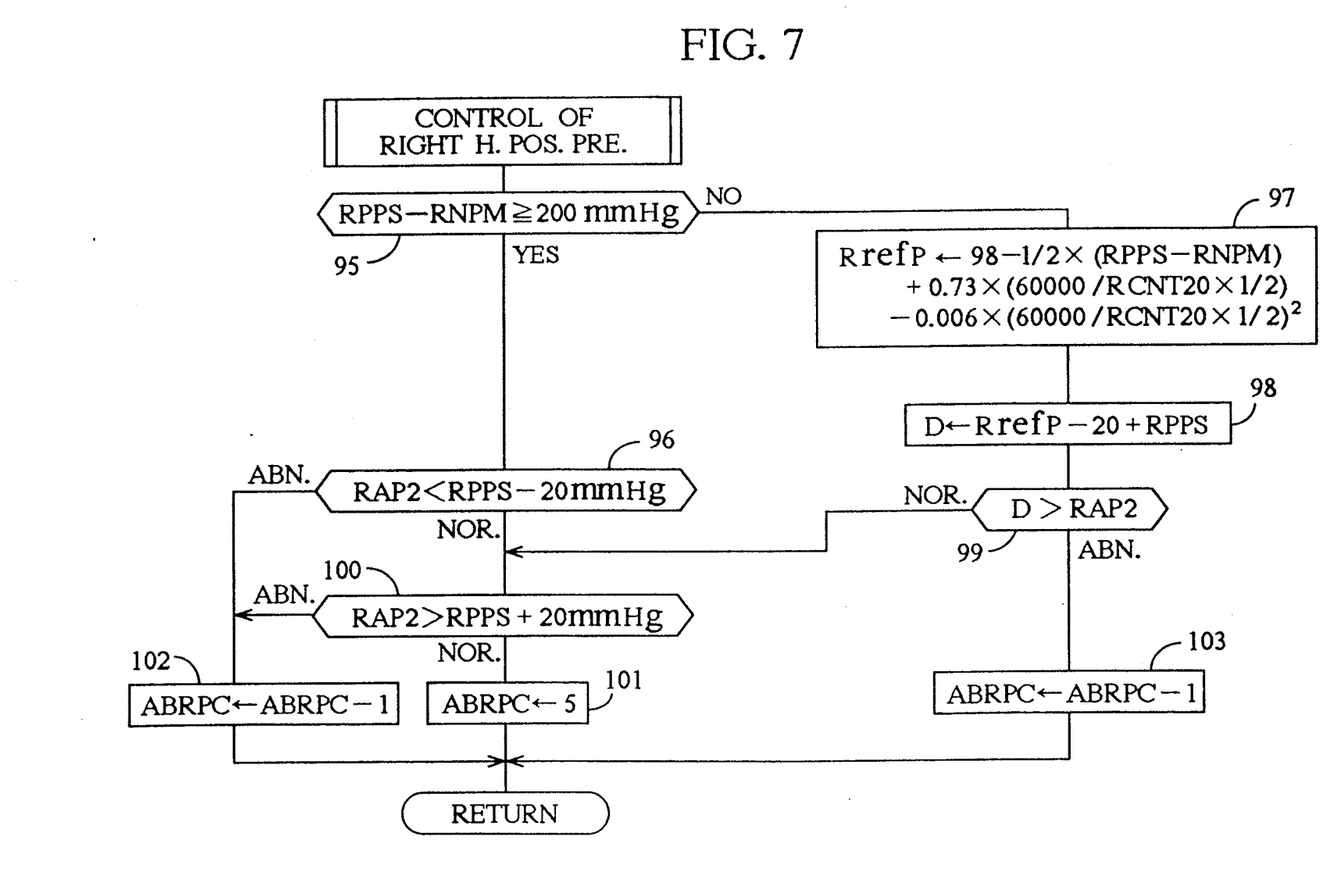

The positive pressure for the right heart is checked in the same manner. If this pressure is normal, the variable ABRPC is 5. If this pressure is regarded as abnormal at five successive decisions, then the variable ABRPC is 0.

The relations of the pressure produced by the pressure pulse generator for the left heart to various variables are shown in FIG. 8. In this case, the difference between the positive pressure and the negative pressure is in excess of 200 mmHg. The normal range of positive pressure values lies between (LPPS−α) and (LPPS+20 mmHg), where LPPS is the preset positive pressure value, and α is obtained by adding allowance value 20 mmHg to the correcting value $L_{ref}P$ for taking the effect of the negative pressure into account. The correcting value $L_{ref}P$ is obtained from the previous negative pressure value LNPM and from the time LCNT20 for which the previous negative pressure was applied. If the pressure produced when 100 ms elapsed since the application of the positive pressure lies within this normal pressure range, then the pressure is regarded as normal. The normal range of negative pressure values lies between (LNPS−20 mmHg) and (LNPS+β), where LNPS is a negative value, and β is obtained by adding allowance value 20 mmHg to the correcting value $L_{ref}N$ for taking the effect of the negative pressure into account. If the pressure produced when 100 ms passed since the application of the negative pressure lies within this normal range, then the pressure is regarded as normal.

After checking the negative pressure for the left heart, the negative pressure for the right heart, the positive pressure for the left heart, and the negative pressure for the right heart, processings for driving a buzzer are performed (steps 68-73). If any one of variables ABLNC, ABRNC, ABLPC, and ABRPC becomes less than 0, then the buzzer is caused to sound. Thus, if any one of the negative pressure for the left heart, the negative pressure for the right heart, the positive pressure for the left heart, and the negative pressure for the right heart is regarded as abnormal at five successive decisions, then the apparatus can inform the outside user of the abnormality. Only when abnormality is detected successively, the outside user is informed of the abnormality to attach importance to the reliability of the diagnosis of abnormality. In the present example, a buzzer is made to sound when abnormality is detected. A backup pulse generator may be provided instead of the buzzer. When abnormality is detected, the pressure pulse generator used usually is switched to the backup pressure pulse generator.

As described thus far, in accordance with the present invention, the pressure range against which pressure is judged to see if it is abnormal is estimated either from the pressure produced immediately before the pressure is switched to other value or from the time for which the previous pressure was applied. Therefore, the pressure obtained at the time to check the pressure can be estimated, irrespective of the pressure obtained before the switch of the pressure and of the time for which the previous pressure was applied. Hence, if the pressure pulses are blunted, or if the pressure is checked at an instant close to the time at which the pressure is switched, no abnormality is detected as long as the pressure pulse generator is not at fault.

What is claimed is:

1. An apparatus for driving a blood pump, comprising:

a pressure pulse generator for producing pressure pulses;

a pressure-detecting means for detecting the pressure produced by the pressure pulse generator;

an estimating means which reads the output value from the pressure-detecting means before the pressure of the pressure pulses is switched to another value and estimates the range of pressures obtained after the switch of the pressure from said output value produced before the switch of the pressure; and a determining means which compares the output value produced from the pressure-detecting means after the switch of the pressure with the pressure range and determines whether the pressure is abnormal.

2. An apparatus for driving a blood pump, comprising:

a pressure pulse generator for producing pressure pulses;

a pressure-detecting means for detecting the pressure produced by the pressure pulse generator;

an estimating means which estimates the pressure range obtained after the pressure is switched to another value from the time for which the pressure pulses were applied; and a determining means which compares the output value produced from the pressure-detecting means after the switch of the pressure with the pressure range and determines whether the pressure is abnormal.

* * * * *